(12) United States Patent
Lehmann et al.

(10) Patent No.: US 9,980,869 B2
(45) Date of Patent: May 29, 2018

(54) PORTABLE INFANT INCUBATOR

(71) Applicant: THE RESEARCH FOUNDATION FOR THE STATE UNIVERSITY OF NEW YORK, Albany, NY (US)

(72) Inventors: Craig Lehmann, Aquebogue, NY (US); John Brittelli, Brookhaven, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 323 days.

(21) Appl. No.: 14/775,139

(22) PCT Filed: Mar. 13, 2014

(86) PCT No.: PCT/US2014/025511
§ 371 (c)(1),
(2) Date: Sep. 11, 2015

(87) PCT Pub. No.: WO2014/159951
PCT Pub. Date: Oct. 2, 2014

(65) Prior Publication Data
US 2016/0030264 A1   Feb. 4, 2016

Related U.S. Application Data

(60) Provisional application No. 61/784,352, filed on Mar. 14, 2013.

(51) Int. Cl.
*A61G 11/00* (2006.01)
*A61M 16/10* (2006.01)
(Continued)

(52) U.S. Cl.
CPC .......... *A61G 11/006* (2013.01); *A61F 7/0053* (2013.01); *A61G 11/005* (2013.01);
(Continued)

(58) Field of Classification Search
CPC .. A61G 11/005; A61G 11/006; A61G 11/007; A61G 11/009; A61G 11/00; A61G 2203/46
See application file for complete search history.

(56) References Cited

U.S. PATENT DOCUMENTS 3,710,791 A * 1/1973 Deaton ................. A61G 10/04
                                                  128/205.26
5,792,041 A   8/1998 Kobayashi et al.
(Continued)

FOREIGN PATENT DOCUMENTS

CN        203366100 U   12/2013
EP          2514399 A2  10/2012

OTHER PUBLICATIONS

International Search Report dated Aug. 14, 2014 issued in PCT/US2014/025511.

*Primary Examiner* — Christine H Matthews
(74) *Attorney, Agent, or Firm* — Scully, Scott, Murphy & Presser, P.C.

(57) ABSTRACT

A portable infant incubator is provided. The incubator has a foldable circumferential wall connected to a base. The foldable circumferential wall has a first configuration folded on a top surface of the base and a second configuration standing from the top surface of the base. A cover is operatively connected to the wall when wall is in the second configuration, to provide a substantially enclosed space with the wall and the top surface of the base. An environmental control device is provided to maintain a predetermined temperature and humidity within the enclosed space. A sensor is provided to acquire environmental data and providing the data to the environmental control device.

15 Claims, 7 Drawing Sheets

(51) Int. Cl.
    *A61M 16/16*    (2006.01)
    *A61F 7/00*     (2006.01)
    *A61M 16/00*    (2006.01)

(52) U.S. Cl.
    CPC ....... *A61G 11/009* (2013.01); *A61M 16/0051* (2013.01); *A61M 16/024* (2017.08); *A61M 16/101* (2014.02); *A61M 16/161* (2014.02); *A61F 2007/006* (2013.01); *A61F 2007/0086* (2013.01); *A61G 2203/46* (2013.01)

(56) References Cited

U.S. PATENT DOCUMENTS

2001/0027267 A1* 10/2001 Jones ................... A61G 11/00
                                                    600/22
2001/0049465 A1* 12/2001 Goldberg ............... A61G 11/00
                                                    600/22
2002/0196141 A1* 12/2002 Boone .................. G08B 29/186
                                                    340/523
2012/0269568 A1* 10/2012 Matsubara ........... A61G 11/006
                                                    403/104

* cited by examiner

PORTABLE INFANT INCUBATOR

CROSS REFERENCE TO RELATED APPLICATIONS

Reference is made to U.S. Provisional Applications Ser. Nos. 61/784,352, filed Mar. 14, 2013 the disclosure of which is incorporated herein by reference in its entirety.

BACKGROUND OF THE DISCLOSURE

The present disclosure relates generally to infant incubators. More specifically, the present disclosure relates to a portable infant incubator.

Current incubators are large, heavy and expensive. Storage of any more than a few of these units is not practical due to space restrictions. In addition the current incubators are bulky and can weigh several hundred pounds, making them difficult to transport from one location to another (requiring a truck with a lift gate) in the event of natural or man-made disaster.

Moreover, infant incubators currently in use are ill suited for the developing world and hard to reach areas, because they are expensive, complex to operate, consist of many parts that break, are heavy, and require an extraordinary amount of space. These devices are not feasible in resource-poor areas where hospital/clinic space and funding is unavailable.

In addition, currently used incubators, when not in use take up large amounts of space making it impossible to store more than a few incubators. Thus, hospitals and clinics are disinclined to have more infant incubators than would be needed on a normal basis. Therefore, additional incubators are not available during a natural or man-made disaster where hospitals may receive a surge of infants due to the evacuation of nearby hospitals.

SUMMARY OF THE DISCLOSURE

According to an exemplary aspect of the present disclosure, a portable infant incubator is provided. The incubator includes a base having a top surface. The incubator further includes a foldable circumferential wall connected to the base. The foldable circumferential wall has a first configuration folded on the top surface of the base and a second configuration standing from the top surface of the base. The incubator further includes a cover operatively connected to the foldable circumferential wall, when the foldable circumferential wall is in the second configuration. Accordingly, a substantially enclosed space is provided by the foldable circumferential wall, the cover and the top surface of the base. The incubator further includes an environmental control device configured to maintain a predetermined temperature and humidity within the enclosed space and a sensor for acquiring environmental data and providing the data to the environmental control device.

The device is a low cost, light weight, foldable infant incubator. It is composed of plexi-glass housing which when not in use will disassemble/fold to about 1/10 its size. The device can be assembles and or disassembled within minutes. It can be stored indefinitely for use at any time in case of natural or man-made disaster requiring the sudden care of numerous infants. The proposed infant incubator will allow for temperature, humidity and oxygen controlled environment. In the event of a power failure there are ventilation ports situated in such a manner that passive exchange of air will be adequate for the infant.

The incubator of the present disclosure contains a monitoring device which will measure and display internal temperature, oxygen concentration and humidity. The monitoring device also initiates an audible alarm when pre-set thresholds are met.

BRIEF DESCRIPTION OF THE DRAWINGS

These and other features, aspects, and advantages of the present disclosure will become better understood with regard to the following description, appended claims, and accompanying drawings wherein:

DETAILED DESCRIPTION OF EXEMPLARY EMBODIMENTS

Detailed embodiments of the present disclosure are described herein; however, it is to be understood that the disclosed embodiments are merely illustrative of the compositions, structures and methods of the disclosure that may be embodied in various forms. In addition, each of the examples given in connection with the various embodiments is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the compositions, structures and methods disclosed herein. References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment.

Figure 1:
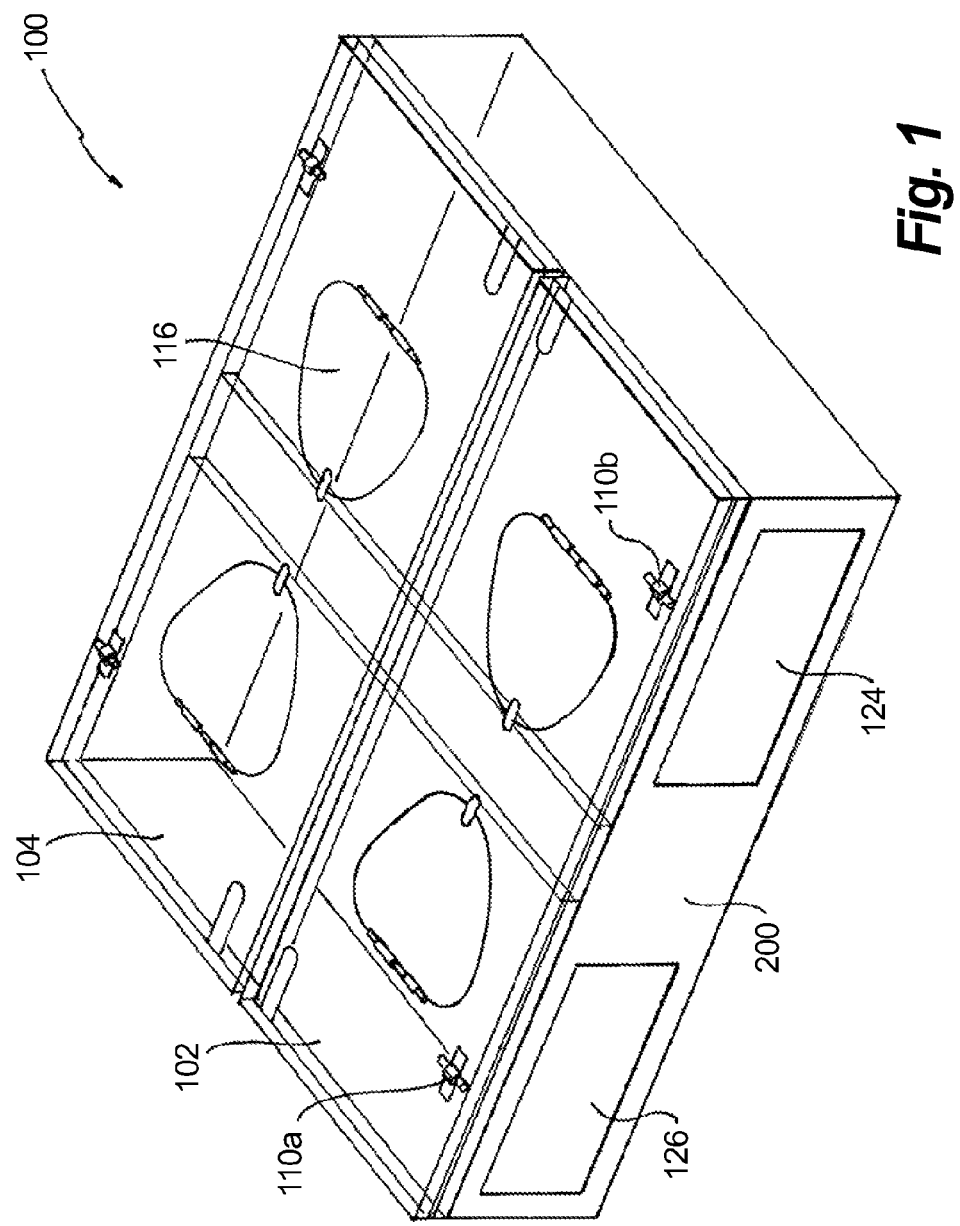
FIG. 1 illustrates an embodiment of the present disclosure in a collapsed configuration.
Figure 2:
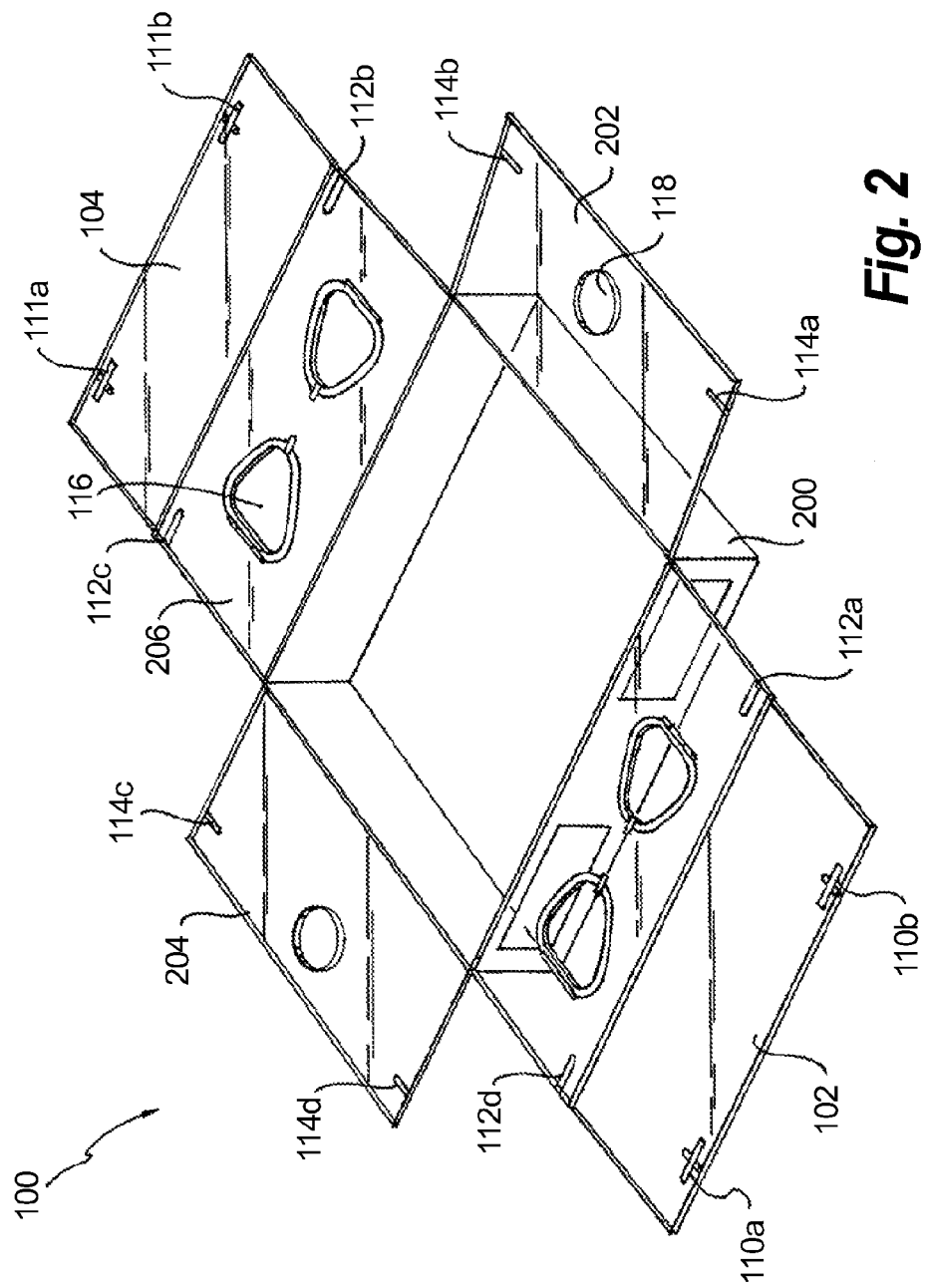
FIG. 2 illustrates an embodiment of the present disclosure in an unfolded configuration.
Figure 3:
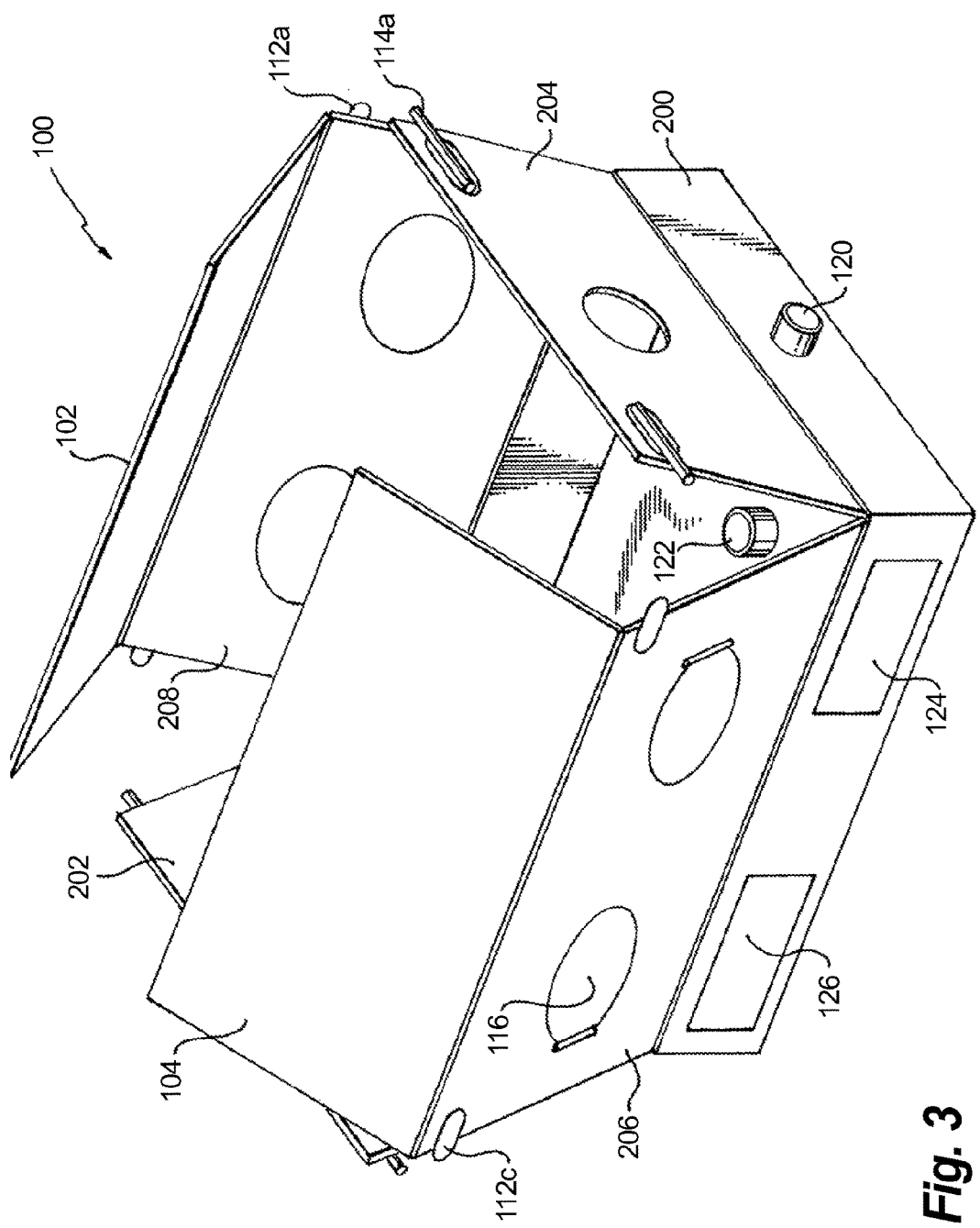
FIG. 3 illustrates an embodiment of the present disclosure in a nearly assembled configuration.

Referring to FIG. 1-3, an embodiment of the present disclosure is a foldable infant incubator 100. In the folded configuration, shown in FIG. 1, an equipment base 200 is covered by front and rear upper panels 102 and 104, respectively. Additionally, the equipment base 200 has a storage compartment 126 and an equipment access hatch 124.

Assembly of the foldable infant incubator 100 of the present disclosure begins by unfolding the upper panels 102 and 104 away from the equipment base 200. Revealing rear panel 206, front panel 208, right side panel 202 and left side panel 204. The rear panel 206 is foldably attached to the equipment base 200 at a bottom edge, and to the rear upper panel 104 at a top edge. Similarly, the front panel 208 is foldably attached to the equipment base 200 at a bottom edge, and to the front upper panel 102 at a top edge. The right side panel 202 and the left side panel 204 are separately attached to the equipment base 200 along bottom edges of the respective panels.

The rear panel 206, front panel 208, right side panel 202 and left side panel 204 can be rotated, around the attached edge, by at least 90° with respect to a top surface of the equipment base 200. Moreover, the front upper panel 102 can be rotated, around its attached edge with front panel 208, by at least 90°, and the rear upper panel 104 can be rotated, around its attached edge with rear panel 206, by at least 90°.

The front panel 208 and rear panel 206 have sliding bolts 112(a-d) disposed at each vertical edge. The sliding bolts 112(a-d) are received by receiving members 114(a-d), respectively, that are disposed at each vertical edge of the right side panel 202 and the left side panel 204. FIG. 3 shows the present embodiment in a state of being assembled. As shown, when the right side panel 202 and the left side panel 204 are positioned relative to the front panel 208 and rear panel 206, such that sliding bolts 112(a-d) are received by respective receiving members 114(a-d), a cuboid enclosure is formed. The front upper panel 102 and rear upper panel 104 form the top portion of the enclosure. The front upper panel 102 has sliding bolts 110(a, b) disposed on an edge opposite of the attached edge, and the rear upper panel 104 has respective receiving members 111(a, b) disposed on an edge opposite of the attached edge. Thus, by way of engagement of the sliding bolts 110(a, b) with the respective receiving members 111(a, b) the enclosure can be closed.

Access to the infant is provided through hand openings 116 provided on the front panel 208 and the rear panel 206. The hand openings 116 include latchable closures. Additionally, the right side panel 202 and the left side panel 204 are provided with ventilation openings 118 for passive air exchange as well.

Figure 4:
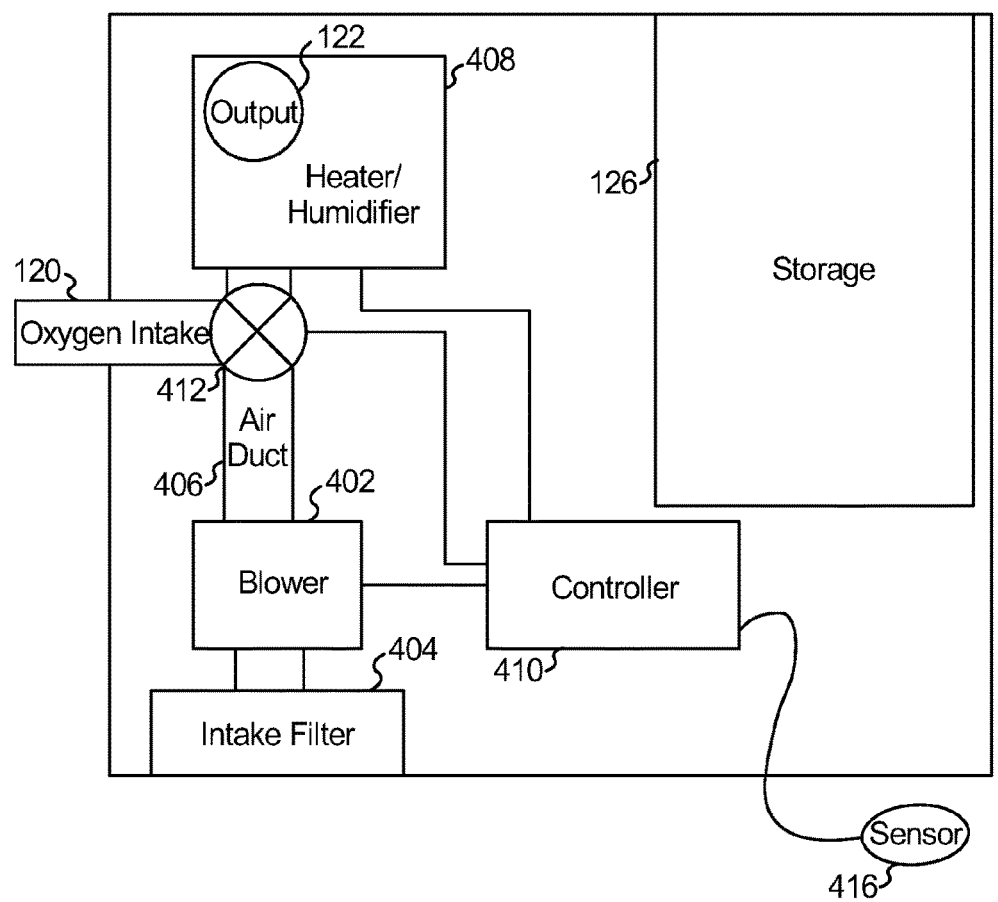
FIG. 4 illustrates an internal view of the equipment base of an embodiment of the present disclosure.

A block representation of the equipment base 200, with internal components, is shown in FIG. 4. The equipment base 200 includes a blower motor 402 for providing ventilation to the enclosure. An air filter 404 is provided on the air intake side of the blower motor 402 to filter out pathogens and dust. The blower motor blows air through a duct 406 to a heater 408, which heats the air to a preset temperature controlled by a controller 410. The controller 410 also controls the operation of the blower motor 402.

The heater 408 can be configured to heat water in order to increase humidity of the air output to the enclosure through output nozzle 122. Alternatively, water may be vaporized by application of ultrasonic energy and introduced into the blown air at the heater 408.

Additionally, a valve 412 actuated by the controller 410, or manually in an embodiment, introduces oxygen ($O_2$) into the blown air for output through the output nozzle 122. The oxygen is supplied by an external source (not shown) coupled to an $O_2$ input nozzle 120.

The controller 410 is coupled to an environmental sensor 416 disposed on a surface of one of the panels 102, 104, 202, 204, 206, 208 forming the enclosure. Alternatively, the environmental sensor 416 may be attachable at an operator-determined position within the enclosure during usage. The environmental sensor 416 is configured to acquire data regarding temperature and humidity within the enclosure. Additionally, the environmental sensor 416 may be further configured, in an embodiment, to acquire data regarding one or more of $O_2$ levels, $CO_2$ levels and other appropriate environmental parameters.

The data acquire by the environmental sensor 416 is transferred to the controller 410, which in turn controls air flow, heater operation, humidification and $O_2$ mixing based on the data.

In an embodiment of the present disclosure, the panels 102, 104, 202, 204, 206, 208 forming the enclosure are constructed of a transparent acrylic plastic (Poly(methyl2-methylpropenoate)), such as Plexiglas. Alternatively, other transparent materials can be used, such as polycarbonate plastics and the like. The equipment base 200 may be fabricated of plastics such as acrylic plastics, polycarbonate plastics. However, since transparency is not required for the equipment base 200, other materials such as non-transparent plastics and metals (stainless steel, aluminum) may be used as well.

Figure 5:
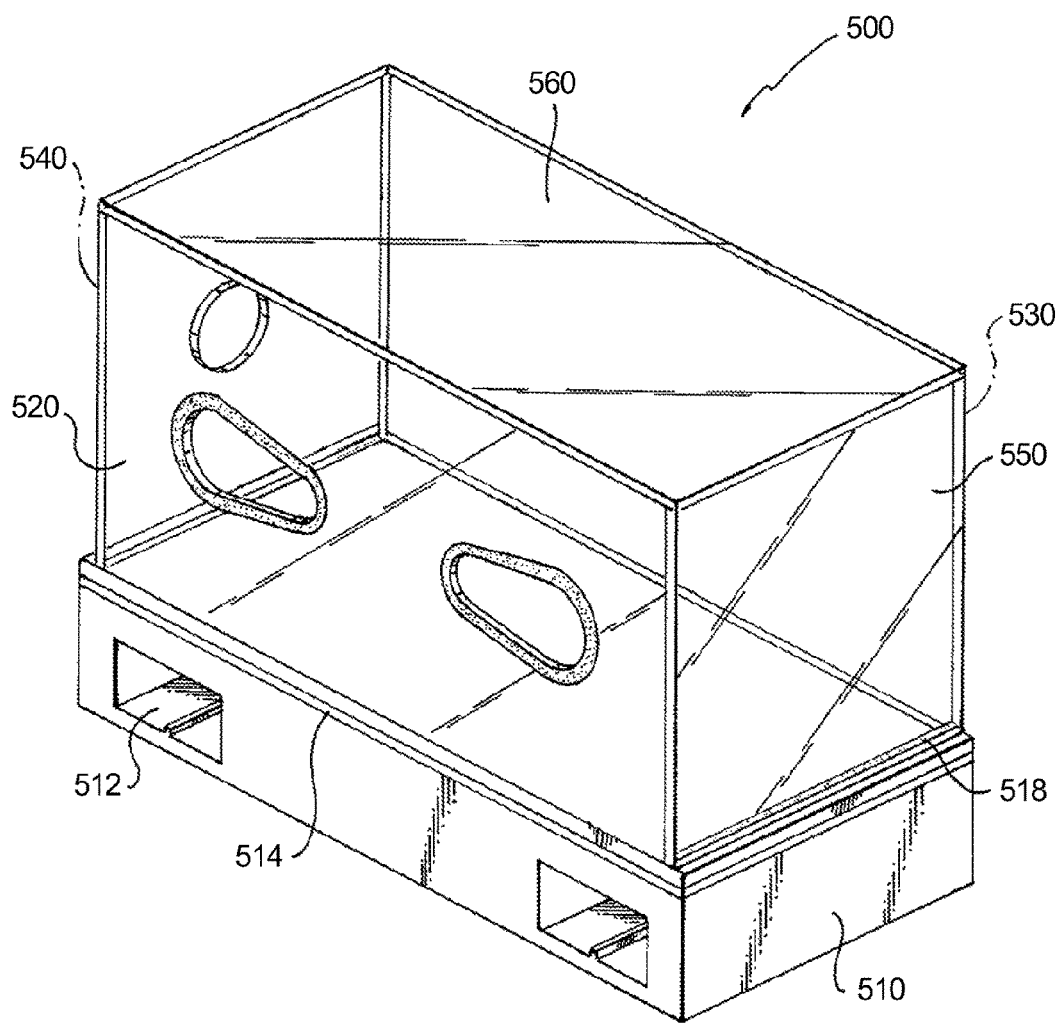
FIG. 5 illustrates another embodiment the present disclosure in a assembled configuration.
Figure 6:
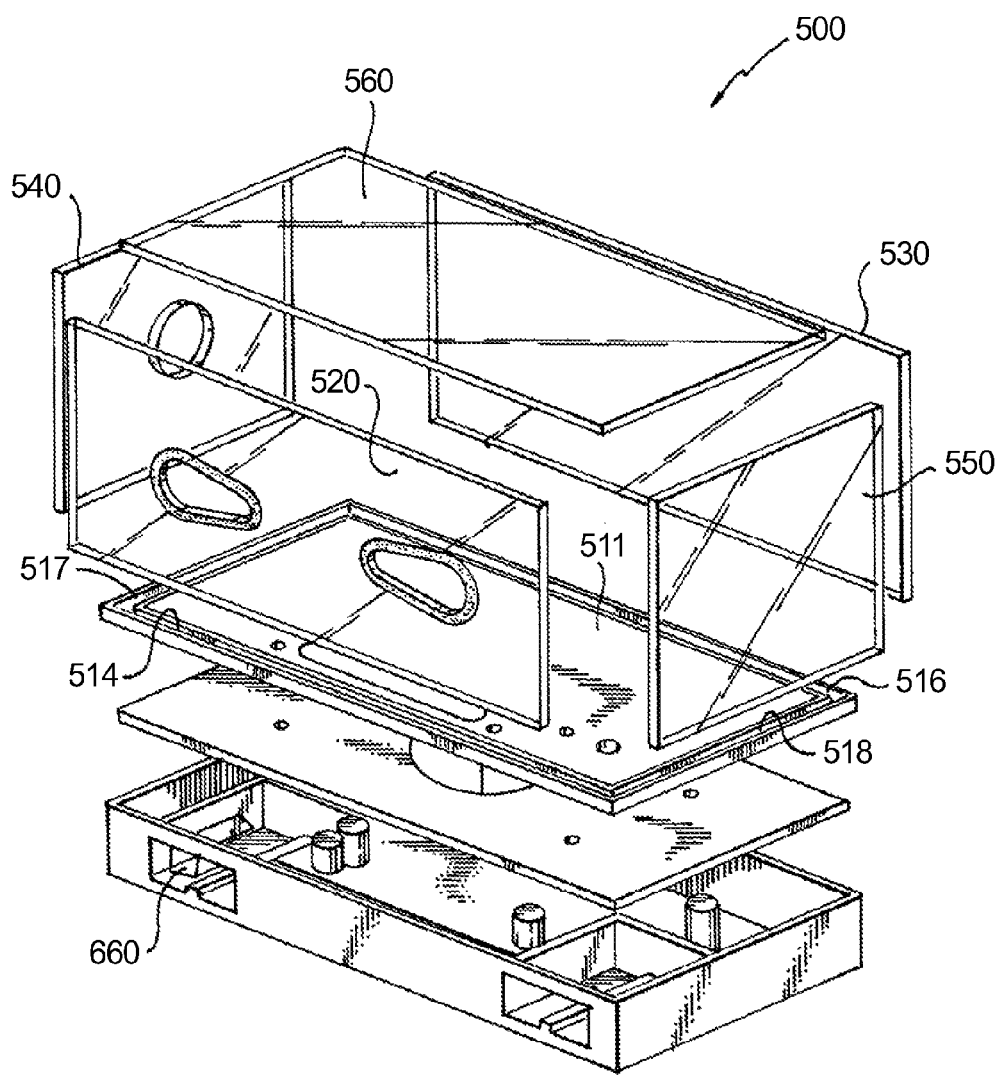
FIG. 6 is an exploded view of the embodiment shown in FIG. 5.

FIGS. 5 and 6 illustrate a foldable infant incubator 500, according to another exemplary embodiment of the present disclosure. The incubator 500 includes a base 510 having a top surface 511, and a foldable circumferential wall connected to the base. The foldable circumferential wall has a first configuration folded or collapsed on the top surface 511 of the base 510 (as shown in FIG. 1) and a second configuration standing from the top surface 511 of the base 510 as shown in FIG. 5.

The circumferential wall is formed by a plurality of panels 520-550 foldably, such as pivotably, connected to the base 510. The panels 520-550 can be manipulated by a user to switch between the first configuration for easy storage and handling and the second configuration when used for an infant. For example, a front panel 520 is pivotably connected to a front edge 514 of the base 510, such that the front panel 520 can be pivoted to stand substantially vertically to the top surface 511 of the base 510. A rear panel 530 is pivotably connected to a rear edge 516 of the base 510, such that the rear panel 530 can be pivoted to stand substantially vertically to the top surface 511 of the base 510. A left panel 540 is pivotably connected to a left side edge 517 of the base 510, such that the left panel 540 can be pivoted to stand substantially vertically to the top surface 511 of the base 510. A right panel 550 is pivotably connected to a right side edge 518 of the base 510, such that the right panel 550 can be pivoted to stand substantially vertically to the top surface 511 of the base 510. When the circumferential wall is in the second configuration, the four panels 520-550 are pivoted to their standing positions, where each panel is fixedly connected to its adjacent panels through sliding bolts and receiving members. However, the foldable feature of the circumferential wall can be implemented through other mechanism. For example, the panels 520-550 can be each inserted into a respective receiving slot formed through the top surface 511 of the base, to therefore stand vertically to the top surface.

The incubator 500 further includes a cover operatively connected to the foldable circumferential wall when the foldable circumferential wall is in the second configuration. Accordingly, a substantially enclosed space is formed by the foldable circumferential wall, the cover and the top surface of the base.

For example, the cover includes a top panel 560, which can be operatively connected to the four standing panels. The top panel 560 can be a stand-alone panel that can be connected to the panels 520-550, such as the top edges of the panels, through pins, clips, clamps and the like. Alternatively, the top panel 560 can be a pivotable extension of any of the panels 520-550; for example, the top panel 560 is pivotably connected to the front panel 520, and dimensioned to substantially cover the area defined by the circumferential wall of the incubator. Alternatively, the top panel 560 can be a multi-part panel, which is formed by operatively connecting the pivotable extensions of two or more of the standing panels 520-550, such as the top panel formed by the front upper panel 102 and the rear upper panel 104 of the incubator 100. Alternatively, the top panel 560 can be a multi-layer panel, which is formed by stacking the pivotable extensions of two or more of the standing panels 520-550; for example, the top panel 560 can be double-layer panel formed by partially or fully stacking a pivotable extension of the front panel 520 and a pivotable extension of the rear panel 530.

Figure 7:
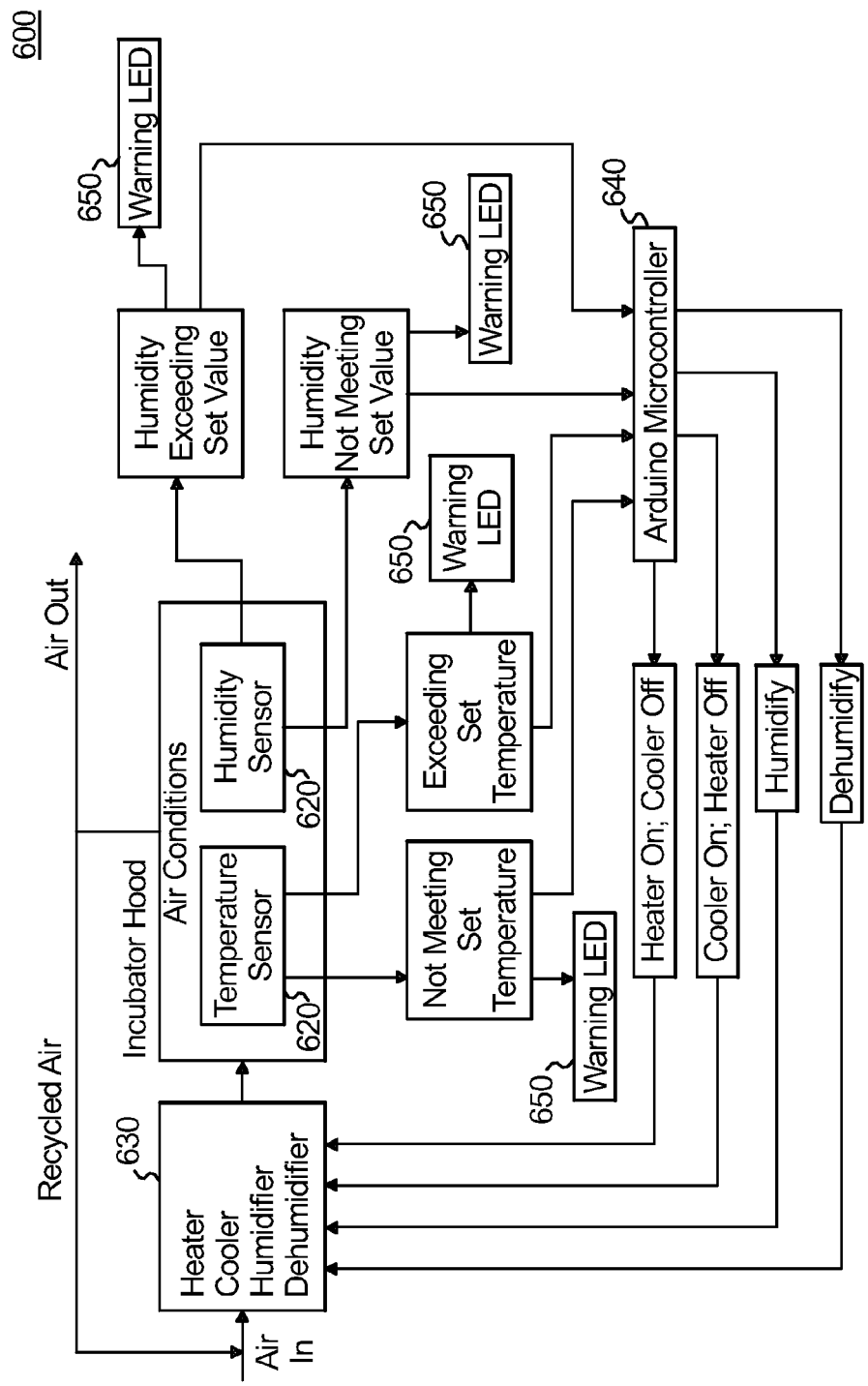
FIG. 7 is a flow diagram of a control system of the incubator shown in FIG. 5.

FIG. 7 illustrates a flow diagram of a control system 600 of the incubator 500. The control system 600 includes an environmental control device 610 configured to maintain a predetermined temperature and humidity within the enclosed space of the incubator 500, and a sensor 620 for acquiring environmental data and providing the data to the environmental control device. For example, the sensor 620 detects the temperature and/or humidity within the enclosed space of the incubator 500.

As shown in FIG. 7, the environmental control device 610 includes a multi-functional member 630, which is capable of functioning as a heater, cooler, humidifier and/or dehumidifier as circumstances require. The environmental control device 610 further includes a controller 640, which is in communication with the multi-functional member 630 and the sensor 620 through wired or wireless communication and configured to process the environmental data acquired by the sensor 620 and send operation instructions to the multi-functional member 630 based on the processing result. For example, the environmental control device 610, including the multi-functional member 630 and the controller 640, can be designed as a module, which can be replaceably and retrofittably disposed within the base 510.

The environmental control device 610 can further include an alarm generator 650 for sending out an alarm if the temperature and/or humidity are not in acceptable ranges. The alarm generator 650 can be in the form of an LED. The alarm generator 650 can be in wired or wireless communication with the controller 640.

The environmental control device 610 can optionally include an oxygen concentrator 660 (shown in FIG. 6). In this case, the base 510 can include a recess 512 for defining a receiving space, in which the oxygen concentrator 660 can be selectively provided. Therefore, depending on the need of the oxygen concentrator 660, it can be added to or removed from the incubator 500. In use, the oxygen concentrator 660 serves to concentrate the oxygen from a gas supply, typically ambient air, to supply an oxygen enriched gas mixture. The oxygen concentrator 660 typically use pressure swing adsorption technology and are used widely for oxygen provision in healthcare applications, particularly where liquid or pressurized oxygen would cause inconvenience or danger, such as in homes or in portable clinics.

Additional units or members, such as the blower 402, the filter 404, the air duct 406 and the valve 412 as described previously, can also be included in a similar manner to the incubator 500. These components can be designed as replaceable and retrofittable modules.

According to an aspect of the claimed disclosure, the maximum temperature of the incubator can be about 40 Celsius degree, the minimum temperature can be about 20 Celsius degree, the maximum temperature of the incubator wall can be about 37.5 Celsius degree, and the minimum temperature of the incubator wall can be about 27.5 Celsius degree. Furthermore, the velocity of air around the incubator can be about 1 m/s and the velocity of air in the incubator can be about 0.002 m/s. The wall thickness of the incubator can be about 0.003175 m, and the surface area of the incubator can be about 1.16 m$^2$. Based on the incubator according to the claimed disclosure, the temperature of an infant can be controlled at about 37 Celsius degree, the water lost by the infant evaporation can be controlled at about 2.09 gH$_2$O/hr and the water lost by infant respiration can be controlled at about 0.43406 gH$_2$O/hr, given that the surface area of the infant is about 0.1973 m$^2$ if modeled as a cylinder.

The incubator according to an aspect of the claimed disclosure can be powered by batteries or an a/c power supply. The batteries can be a part of a modular unit and can power the incubator up to 5 hours. The batteries can be recharged when the incubator is powered by the a/c power supply.

The incubator according to an aspect of the claimed disclosure can have a maximum width of about 15 inches, a maximum length of about 30 inches and a maximum height of about 20 inches. The incubator according to an aspect of the claimed disclosure can have an overall weight of about less than 28 pounds.

The incubator according to an aspect of the claimed disclosure can be easily maintained, and the components of the incubator can be easily replaced and sanitized between uses. The incubator can be used in an environment of temperatures between of 57.2 to 105° F.

The incubator according to an aspect of the claimed disclosure provides certain advantages. For example, the incubator is collapsible and stackable to require minimal storage space. The modular design of the subcomponents, such as the heating and cooling unit, renders the subcomponents suitable for use, even during winter and summer seasons.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A portable infant incubator comprising:
    a base having a top surface;
    a foldable circumferential wall connected to the base, the foldable circumferential wall comprising a first configuration folded on the top surface of the base and a second configuration standing from the top surface of the base;
    a cover operatively connected to the foldable circumferential wall when the foldable circumferential wall is in the second configuration, thereby providing a substantially enclosed space with the foldable circumferential wall and the top surface of the base;
    an environmental control device configured to maintain a predetermined temperature and humidity within the enclosed space; and
    a sensor for acquiring environmental data and providing the data to the environmental control device, wherein the circumferential wall comprises:
    a front panel foldably connected to a front edge of the base;
    a rear panel foldably connected to a rear edge of the base;
    a left panel foldably connected to a left edge of the base; and a right panel foldably connected to a right edge of the base, wherein, when the circumferential wall is in the second configuration, the front panel, the rear panel, the left panel and the right panel are manipulated to stand substantially vertically with respect to the top surface of the base, and wherein the cover comprises:
a front upper panel pivotably connected to the front panel; and
a rear upper panel pivotably connected to the rear panel, wherein when the circumferential wall is in the second configuration, the front upper panel and the rear upper panel are fixedly connected to each other through a sliding bolt and a receiving member.

2. The portable infant incubator of claim 1, wherein when the circumferential wall is in the second configuration, each of the front panel, the rear panel, the left panel and the right panel is fixedly connected to an adjacent one of the front panel, the rear panel, the left panel and the right panel through a sliding bolt and a receiving member.

3. The portable infant incubator of claim 1, wherein the cover comprises a top panel fixedly connectable to the front panel, the rear panel, the left panel and the right panel.

4. The portable infant incubator of claim 1, further comprising sealable hand openings in the front panel and the rear panel.

5. The portable infant incubator of claim 1, wherein the environmental control device comprises:
a multi-functional member configured to heat, cool, humidify and/or dehumidify the enclosed space; and
a controller in communication with the multi-functional member and the sensor, wherein the controller is configured to process the environmental data acquired by the sensor and send an operation instruction to the multi-functional member based on a result of the processing.

6. The portable infant incubator of claim 5, wherein the environmental control device further comprises an air blower for introducing ambient air into the enclosed space and an air filter filtering the air introduced by the air blower.

7. The portable infant incubator of claim 5, wherein the environmental control device further comprises an oxygen concentrator for supplying an oxygen enriched gas mixture.

8. The portable infant incubator of claim 5, wherein the environmental control device further comprises an alarm generator in communication with the controller, the alarm generator being configured to generate an alarm when the predetermined temperature and humidity within the enclosed space are not satisfied.

9. The portable infant incubator of claim 1, wherein the base has a recess for defining an inner space and the environmental control device is slidably disposed within the inner space.

10. The portable infant incubator of claim 1, wherein the circumferential wall is made of a transparent plastic selected from a group consisting of acrylic plastic and polycarbonate plastic.

11. A portable infant incubator comprising:
a base having a top surface;
a foldable circumferential wall connected to the base, the foldable circumferential wall comprising a first configuration folded on the top surface of the base and a second configuration standing from the top surface of the base;
a cover operatively connected to the foldable circumferential wall when the foldable circumferential wall is in the second configuration, thereby providing a substantially enclosed space with the foldable circumferential wall and the top surface of the base;
an environmental control device configured to maintain a predetermined temperature and humidity within the enclosed space; and
a sensor for acquiring environmental data and providing the data to the environmental control device,
wherein the environmental control device comprises:
a multi-functional member configured to heat, cool, humidify and/or dehumidify the enclosed space; and
a controller in communication with the multi-functional member and the sensor, wherein the controller is configured to process the environmental data acquired by the sensor and send an operation instruction to the multi-functional member based on a result of the processing, and
wherein the environmental control device further comprises an air blower for introducing ambient air into the enclosed space and an air filter filtering the air introduced by the air blower.

12. The portable infant incubator of claim 11, wherein the environmental control device further comprises an oxygen concentrator for supplying an oxygen enriched gas mixture.

13. The portable infant incubator of claim 11, wherein the environmental control device further comprises an alarm generator in communication with the controller, the alarm generator being configured to generate an alarm when the predetermined temperature and humidity within the enclosed space are not satisfied.

14. The portable infant incubator of claim 11, wherein the base has a recess for defining an inner space and the environmental control device is slidably disposed within the inner space.

15. The portable infant incubator of claim 11, wherein the circumferential wall is made of a transparent plastic selected from a group consisting of acrylic plastic and polycarbonate plastic.

* * * * *